United States Patent [19]

Terndrup et al.

[11] Patent Number: 4,917,672
[45] Date of Patent: Apr. 17, 1990

[54] SHIELD FOR AN HYPODERMIC SYRINGE INJECTION NEEDLE

[76] Inventors: Thomas E. Terndrup, 1752 Berwyn Rd., LaFayette, N.Y. 13084; Brian R. Terndrup, R.D. 1 Box 142, Ebensburg, Pa. 15931

[21] Appl. No.: 324,701

[22] Filed: Mar. 17, 1989

[51] Int. Cl.⁴ ............................................. A61M 5/32
[52] U.S. Cl. .................................... 604/192; 604/198; 604/263
[58] Field of Search ................ 604/192, 187, 198, 263

[56] References Cited

U.S. PATENT DOCUMENTS

| | | | |
|---|---|---|---|
| 1,944,553 | 6/1929 | Freund | 604/275 |
| 2,876,770 | 10/1955 | White | 604/198 |
| 3,134,380 | 2/1962 | Armao | 604/198 |
| 4,664,654 | 5/1987 | Strauss | 604/198 |
| 4,725,267 | 2/1988 | Vaillancourt | 604/192 |
| 4,735,618 | 4/1988 | Hagen | 604/192 |
| 4,747,829 | 5/1988 | Jacob | 604/110 |
| 4,775,369 | 10/1988 | Schwartz | 604/263 |

Primary Examiner—John D. Yasko
Attorney, Agent, or Firm—Shlesinger & Myers

[57] ABSTRACT

A shield for the injection needle of an hypodermic syringe, comprises a movable shield sleeve having a channel extending therethrough from the top to the bottom and having upper and lower portions for normally positioning the sharpened end of the injection needle in the upper portion. The sleeve includes a plunger having an opening alignable with the channel. The plunger is movable between a normal blocking position in which the plunger opening is misaligned with respect to the channel, and an aligned position in which the plunger opening is aligned with respect to the channel, to permit the needle to move through the plunger opening, thereby permitting the needle to be exposed a substantial distance below the bottom of the sleeve for purposes of injection. Automatic means associated with the syringe and the sleeve permit the needle to be automatically retracted into the sleeve upper portion, after the needle has been exposed a substantial distance below the bottom of the sleeve for injection. Automatic means is also provided for automatically bringing the plunger to the normal blocking position subsequent to retraction of the needle in the sleeve and from the plunger opening.

16 Claims, 2 Drawing Sheets

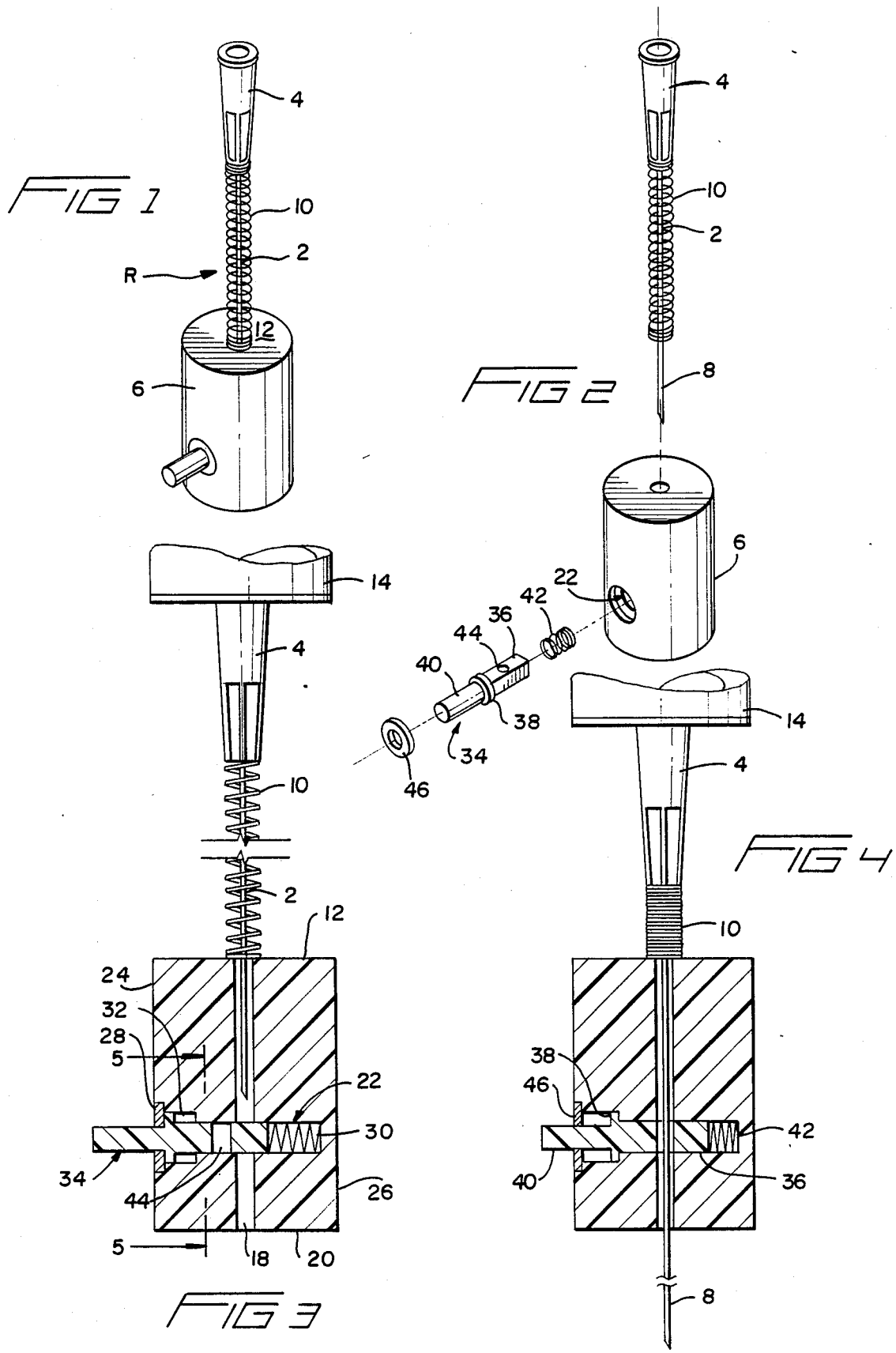

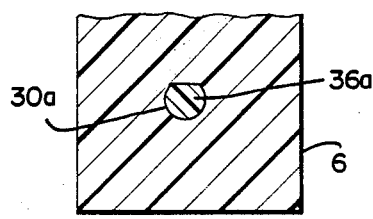
FIG 5
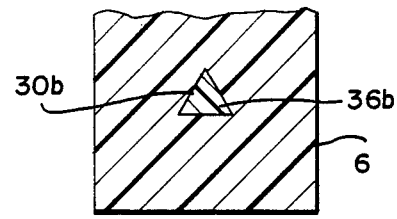
FIG 6
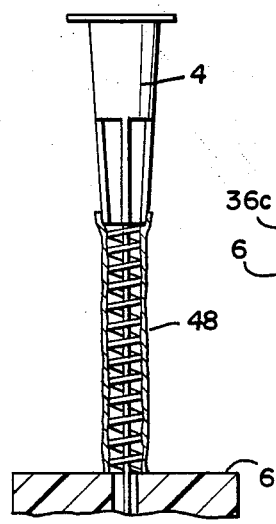
FIG 8
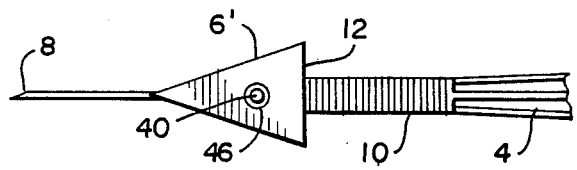
FIG 7
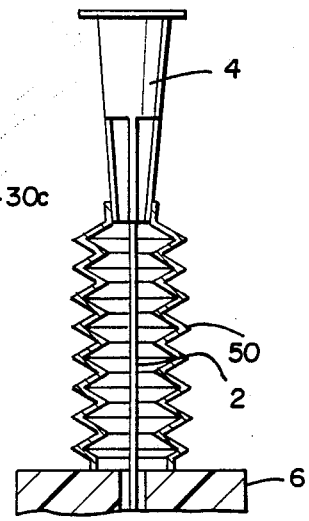
FIG 9
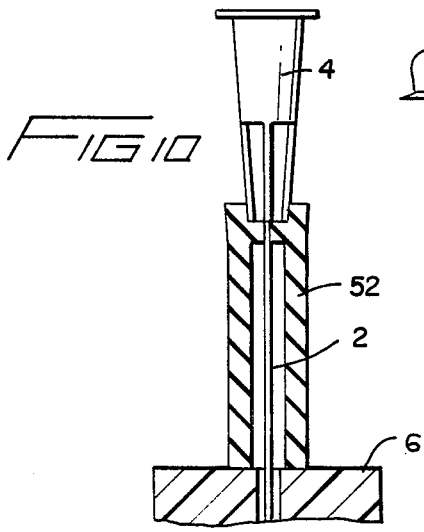
FIG 10
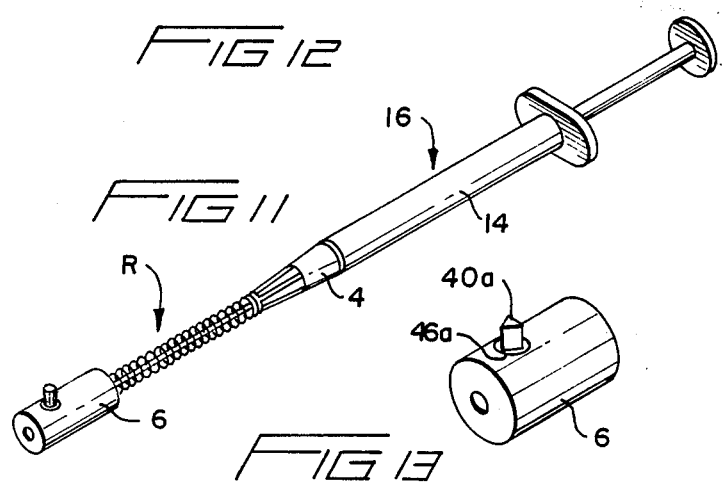
FIG 12
FIG 11
FIG 13

SHIELD FOR AN HYPODERMIC SYRINGE INJECTION NEEDLE

FIELD OF THE INVENTION

The present invention relates generally to devices for providing a shield for an hypodermic syringe needle and more particularly to devices for maintaining the sharpened end of an hypodermic syringe needle automatically shielded at all times under normal use. Normal use to include injection, aspiration, and proper disposal.

BACKGROUND OF THE INVENTION

Contaminated needles may contain fluids or blood products capable of transmitting diseases to the victims of accidental exposure. This is of particular concern to health care workers, including nurses, doctors, medical technicians and any worker handling contaminated needles, such as medical waste handlers. Many diseases may be transmitted from an accidental needle puncture, including hepatitis B, cytomegalovirus and potentially Human Immunodeficiency Virus (previously known as AIDS).

Although shields for hypodermic syringe needles are well known in the art, there is a need for a type of shield which automatically shields an exposed needle without intervention from the user. The user is at a high risk from accidental puncture when he or she has to insert a cap on an exposed needle, unfold a folded enclosure or slide an enclosure over the needle.

OBJECTS AND SUMMARY OF THE INVENTION

It is therefore an object of the present invention to provide a shield for an hypodermic syringe needle.

It is also an object of the present invention to provide a shield for an hypodermic syringe needle which automatically shields the sharpened end of the needle.

It is still an object of the present invention to provide a shield for an hypodermic syringe needle which prevents the sharpened end of the needle from accidental exposure.

It is a further object of the present invention to provide a shield for an hypodermic syringe needle which requires a deliberate act from the user to expose the sharpened end of the needle.

It is an object of the present invention to provide a shield for an hypodermic syringe needle which maintains the needle shielded from the user even during normal use.

It is also an object of the present invention to provide a shield for an hypodermic syringe needle which automatically retracts the sharpened end of the needle into the shield after being exposed.

It is still an object of the present invention to provide a shield for an hypodermic syringe needle which automatically blocks the sharpened end of the needle from exposure once the needle has retracted into the shield after use.

It is a further object of the present invention to provide a shield for an hypodermic syringe needle for protecting health care workers from accidental needle punctures attendant with exposed needles.

It is yet an object of the present invention to provide a shield for an hypodermic syringe needle for preventing transmission of diseases through contact with contaminated needles.

It is an object of the present invention to provide a shield for an hypodermic syringe needle which minimizes dulling of the sharpened end of the needle while in the shielded position.

It is a further object of the present invention to provide a shield for an hypodermic needle which is relatively easy to manufacture.

It is still an object of the present invention to provide a shield for an hypodermic syringe needle which is made from relatively inexpensive materials.

In summary, the present invention provides a shield for an hypodermic syringe needle which maintains the sharpened end of the needle shielded at all times under normal use.

DESCRIPTION OF THE DRAWINGS

FIG. 1 is a perspective view of the present invention, shown secured to an hypodermic syringe needle.

FIG. 2 is a perspective, exploded view of FIG. 1.

FIG. 3 is a side elevational, broken-away, partly in cross-section view of the present invention, taken along a longitudinal axis in FIG. 1, showing an hypodermic syringe needle in the normal shielded position.

FIG. 4 is a side elevational, broken-away view, partly in cross-section, view of the present invention, similar to FIG. 3, showing an hypodermic syringe needle in the exposed position.

FIGS. 5, 6 and 7 are sectional, broken-away views, taken along line 5—5 in FIG. 3, showing various embodiments of a plunger used in the present invention.

FIGS. 8, 9 and 10 are side elevational, broken-away, partly in cross-section, views taken from FIG. 1, showing the various embodiments of a spring means used in the present invention.

FIG. 11 is a perspective view of an hypodermic syringe utilizing the present invention.

FIG. 12 is a side elevational, broken-away view, showing an embodiment of a sleeve used in the present invention.

FIG. 13 is a perspective view showing an embodiment of a pushbutton and a retainer washer used in the present invention.

DESCRIPTION OF THE INVENTION

FIGS. 1, 2, 3, 4, 11 AND 12

A hypodermic syringe needle assembly R comprises an injection needle 2 secured to a hub 4. A shield sleeve 6 encloses the sharpened end 8 of the needle 2. A wire spring 10, secured by conventional means to the hub 4 and top surface 12 of sleeve 6, is disposed around the needle 2. The hub 4 is secured by conventional means to barrel 14 of syringe 16, as best shown in FIG. 11. The sleeve 6 is preferably made from lightweight plastic materials.

The sleeve 6 includes a channel 18 extending axially from the top surface 12 to the bottom surface 20 of sleeve 6. The sharpened end 8 of the needle 2 normally resides within the channel 18 when not being used to protect the user from accidental puncture. The diameter of the channel 18 preferably will vary, depending on the gauge of the needle 2 which is used. The sleeve 6 further includes an opening 22, extending transversely to the axis of the sleeve 6 from an outer surface 24 and stopping short of the opposite surface 26 and intersecting the channel 18. The opening 22 includes a larger size opening 28 adjacent the surface 24, a smaller size opening 30 which intersects the channel 18, and an intermediate size opening 32 positioned between the opening 28 and the opening 30.

The sleeve 6, although shown as cylindrical, can be of a different shape. As best shown in FIG. 12, another embodiment of sleeve 6 is indicated as 6' which is wedge-shaped, tapering downwardly from the top surface 12 to the bottom 20. The wedge shape advantageously permits the user to orient the needle 2 at a small angle relative to a patient's vein, as in drawing blood.

A plunger 34 slidably fits within the opening 22. The plunger 34 includes a shank portion 36 which slidably fits within opening 30, a pushbutton portion 40 which extends beyond the opening 22 and surface 24, and an annular ridge 38, disposed intermediate the shank portion 36 and the pushbutton portion 40, which annular ridge 38 fits within the opening 32. The shank portion 36 includes a transverse opening 44 which is alignable with the channel 18. The opening 44 preferably will have the same size as the channel 18. The plunger 34 is preferably made from plastic materials with enough strength for resisting piercing by the sharpened end 8 of the needle 2, but with sufficient resiliency for minimizing dulling of the sharpened end 8 of the needle 2, from inadvertent contacts between the plunger 34 and the needle 2.

The plunger 34 is installed within the opening 22 by positioning a spring 42 at the bottom of the opening 22, inserting the shank portion 36 into the opening 30, the ridge 38 into the opening 32, and securing, by conventional means, a retainer washer 46 into the opening 28. The ridge 38 is then movable between the retainer washer 46 and a shoulder 47 at the bottom of the opening 32 when the plunger 34 is depressed into the opening 22. The spring 42 has enough force to keep the ridge 38 pushing against the retainer washer 46 when no force is applied to the pushbutton portion 40, so as to maintain the opening 44 normally misaligned with the channel 18, as best shown in FIG. 3. This is the normal blocking position of plunger 23. When force is applied to the pushbutton portion 40 to depress the plunger 34, the spring 42 is compressed, and the opening 44 aligns with the channel 18, when the ridge 38 reaches the bottom of opening 32, as best shown in FIG. 4. This is the aligned position of the plunger 34 for permitting the needle 2 to extend a substantial distance beyond the bottom surface 20 of the sleeve 6. The compressed spring 42 is designed to automatically reposition the plunger 34 to its normal blocking position when force is removed from the pushbutton portion 46 and when the needle 2 is retracted to its shielded position, as best shown in FIG. 3.

FIGS. 5, 6, 7 AND 13

The shank portion 36 of plunger 34 and cooperating opening 30 are appropriately shaped so as to provide alignment means for preventing the opening 44 from shifting about the longitudinal axis of the plunger 34 when the pushbutton portion 40 is depressed. A few examples of alignment means are depicted in FIGS. 5, 6 and 7. As shown in FIG. 5, the shank portion 36a and the corresponding opening 30a are circular segments. The shank portion 36b and the corresponding opening 30b are shown as triangles in FIG. 6. The shank portion 36c and the corresponding opening 30c are shaped as squares in FIG. 7.

Alternatively, the retainer washer 46 and the pushbutton portion 40 may be appropriately shaped to provide the alignment means for the opening 44 and the channel 18. For example, pushbutton portion 40a and opening of the retainer washer 46a are shown triangular in FIG. 13.

Further, the ridge 38 and the corresponding opening 32 may be provided with the appropriate cooperating shapes, similar to those shown in FIGS. 5, 6 and 7, to prevent the plunger 34 from pivoting about its axis and thereby misaligning the opening 44 with the channel 18 when the plunger 34 is depressed.

As will be understandable to a person skilled in the art, the shank portion 36 and the corresponding opening 30, the pushbutton portion 34 and the retainer washer 46 opening, and the ridge 38 and the corresponding opening 32, can be any shape sufficient to prevent rotational movement of the plunger 34 relative to the opening 22.

FIGS. 8, 9 AND 10

The spring 10 preferably can be of several forms. The spring 10 functions to retract the needle 2 into its normal shielded position, as best shown in FIG. 3, after it has been exposed, as best shown in FIG. 4. Therefore, any spring means with adequate restoring force when compressed to retract the needle 2 into its normal shielded position will be sufficient. One embodiment of the spring 10 includes an outer covering 48 made of flexible material, as best shown in FIG. 8. Another embodiment is a bellows 50, made of plastic or other suitable material with sufficient bias, as best shown in FIG. 9. Still another embodiment is a foam rubber 52, as best shown in FIG. 10.

OPERATION

The sharpened end 8 of the needle 2 is normally within the sleeve 6, as best shown in FIG. 3. The plunger 34 is in its normal blocking position when the opening 44 is offset from and not in communication with the channel 18. In this manner, the sharpened end 8 of the needle 2 cannot be accidentally exposed, without any deliberate action from the user. If the user attempts to push the needle 2 through the sleeve 6, without depressing the plunger 34, the solid portion of the shank portion 36 will block the path of the needle 2. Dulling of the sharpened end 8 of the needle 2, by contact with the shank portion 36, is minimized, since the plunger 34 is preferably made from plastic materials with impact absorbing qualities.

To expose the needle 2 for injection, the user rests the bottom surface 20 of the sleeve 6 on the patient, depresses the pushbutton 40 until the ridge 38 contacts the bottom of the opening 32, to align the opening 44 with the channel 18, and pushes the needle toward the patient. Once the needle 2 has gone past the opening 44 toward the patient, the user releases the pressure on the plunger 34. The needle 2 locks the plunger 34 in place and maintains the opening 44 in substantial alignment with the channel 18, as best shown in FIG. 4. The spring 42 at the bottom of the opening 22 is compressed. The spring 10 associated with the sleeve 6 and the hub 4 is compressed, as the user pushes the needle 2 into the patient. The design of the sleeve 6 and the spring 10 allows the needle 2 to protrude a substantial distance beyond the bottom surface 20 to enable the user to perform the injection.

After the content of the syringe has been injected or fluid aspirated, the user withdraws the needle 2 from the patient. Since the spring 10 is under compression, the sleeve 6 stays in contact with the patient, advantageously keeping the sharpened end 8 of the needle 2 shielded from the user, as the needle 2 is retracted. As soon as the sharpened end 8 of the needle 2 goes past the opening 44, the spring 42, which has been under tension, pushes the plunger 34 to its normal blocking position. Therefore, throughout the entire injection process, the sharpened end 8 of the needle 2 is advantageously never exposed to the user. This way, the user is not exposed to the risk of accidental puncture from a contaminated needle.

For drawing blood from a patient, the embodiment of the invention, as best shown in FIG. 12, is preferably used. Since the sleeve 6' is wedge shaped, positioning the needle 2 at the appropriate angle relative to the vein of the patient is made much easier. Exposure of the sharpened end 8 of the needle 2 is only minimal, just enough for the user to position the sharpened end 8 into the vein of the patient. After the blood has been drawn, the user permits the spring 10 to automatically retract the needle 2 into the sleeve 6', while the sleeve 6' is held against the patient, thereby minimizing any risk of accidental puncture from the needle 2.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

We claim:
1. A shield for the injection needle of an hypodermic syringe, comprising:
(a) a movable shield sleeve having top, bottom and sides;
(b) said sleeve including a channel extending therethrough from said top to said bottom and having upper and lower portions for normally positioning the sharpened end of the injection needle in said upper portion;
(c) said sleeve including an opening extending from one side of said sleeve and intersecting said channel and stopping short of the other side of said sleeve and positioned between said upper and lower portions;
(d) said sleeve opening having a plunger positioned therein;
(e) said plunger having an opening therein alignable with said channel;
(f) said plunger being movable between a normal blocking position in which said plunger opening is misaligned with respect to said channel, and an aligned position in which said plunger opening is aligned with respect to said channel;
(g) means for shifting said plunger in said sleeve opening so as to move said plunger opening from said normal blocking position to said aligned position to permit said needle to move through said plunger opening, thereby permitting said needle to be exposed a substantial distance below said bottom of said sleeve for purposes of injection;
(h) automatic means associated with said syringe and said sleeve on said top and movable therewith for permitting said sleeve to move relative to said needle to permit said needle to be automatically retracted into said sleeve upper portion after said needle has been exposed a substantial distance below said bottom of said sleeve for injection; and
(i) automatic means for automatically bringing said plunger to said normal blocking position subsequent to retraction of said needle in said sleeve and from said plunger opening.

2. A shield, as in claim 1, wherein:
(a) said sleeve opening is transverse to said channel.

3. A shield, as in claim 1, wherein:
(a) said plunger includes means for preventing rotational movement of said plunger when said plunger is moved within said sleeve opening.

4. A shield, as in claim 3, wherein:
(a) said plunger cross-section and the respective sleeve opening are angular.

5. A shield, as in claim 1, wherein:
(a) said plunger includes stop means for positively
(a) said plunger includes stop means for positively aligning said plunger opening with said channel when said plunger is moved from said normal blocking position to said aligned position.

6. A shield, as in claim 5, wherein:
(a) said plunger includes a ridge;
(b) said sleeve opening includes a shoulder cooperating with said ridge; and
(c) the distance between said plunger opening and said channel when said plunger is in said normal blocking position is substantially equal to the distance between said ridge and said shoulder, such that when said ridge contacts said shoulder, said plunger opening aligns with said channel.

7. A shield, as in claim 1, wherein:
(a) said shifting means is a pushbutton portion of said plunger disposed outside said sleeve.

8. A shield, as in claim 1, wherein:
(a) said plunger automatic means includes a spring disposed within said sleeve opening.

9. A shield, as in claim 8, wherein:
(a) said sleeve opening includes a bottom; and
(b) said spring is disposed at said bottom of said sleeve.

10. A shield, as in claim 1, wherein:
(a) said automatic means associated with said sleeve and said syringe includes spring means.

11. A shield, as in claim 10, wherein:
(a) said spring means is in the form of bellows.

12. A shield, as in claim 10, wherein: (a) said spring means is foam rubber.

13. A shield, as in claim 10, wherein:
(a) said spring means is a metal wire spring.

14. A shield, as in claim 13, wherein:
(a) said spring means includes an outer covering.

15. A shield, as in claim 1, wherein:
(a) said sleeve is wedge-shaped.

16. A shield, as in claim 15, wherein:
(a) said wedge-shaped sleeve includes a top and a bottom; and
(b) said wedge-shaped sleeve tapers from said top to said bottom.

* * * * *